(12) United States Patent
Braun et al.

(10) Patent No.: US 10,181,074 B2
(45) Date of Patent: Jan. 15, 2019

(54) POSITIONING OF AN EXAMINATION TABLE RELATIVE TO A MEDICAL IMAGING APPARATUS

(71) Applicants: Christoph Braun, Rosenheim (DE); Thilo Hannemann, Erlangen (DE); Johann Uebler, Nürnberg (DE)

(72) Inventors: Christoph Braun, Rosenheim (DE); Thilo Hannemann, Erlangen (DE); Johann Uebler, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 692 days.

(21) Appl. No.: 14/854,362

(22) Filed: Sep. 15, 2015

(65) Prior Publication Data

US 2016/0074004 A1     Mar. 17, 2016

(30) Foreign Application Priority Data

Sep. 16, 2014   (DE) .................. 10 2014 218 558

(51) Int. Cl.
*A61B 6/00* (2006.01)
*G06K 9/00* (2006.01)
(Continued)

(52) U.S. Cl.
CPC .......... *G06K 9/00355* (2013.01); *A61B 6/032* (2013.01); *A61B 6/0457* (2013.01);
(Continued)

(58) Field of Classification Search
CPC ......... A61B 6/00; A61B 6/0492; A61B 6/467; A61B 6/469; A61B 6/488
See application file for complete search history.

(56) References Cited

U.S. PATENT DOCUMENTS 7,433,503 B2 * 10/2008 Cherek ................ A61B 5/0555
378/4
9,028,144 B2 *  5/2015 Choi ...................... A61B 6/032
378/205
(Continued)

FOREIGN PATENT DOCUMENTS

| CN | 1476812 A      | 2/2004  |
|----|----------------|---------|
| CN | 103845067      | 6/2014  |
| DE | 10109219 A1    | 9/2002  |
| DE | 102007017794 B3 | 12/2008 |

OTHER PUBLICATIONS

German Office Action for related German Application No. 10 2014 218 558.0, dated May 7, 2015, with English Translation.
(Continued)

*Primary Examiner* — Thomas R Artman
(74) *Attorney, Agent, or Firm* — Lempia Summerfield Katz LLC (57) ABSTRACT

The automated positioning of an examination table relative to a medical-technical imaging installation is provided. A camera image is frozen by a first user interaction. Reference information is defined in the frozen camera image by a second user interaction. An examination table or medical-technical imaging installation is moved with the aid of a positioning system based on congruence between the reference location information with a recording region of the medical-technical imaging installation.

18 Claims, 4 Drawing Sheets

(51) Int. Cl.
*A61B 6/04* (2006.01)
*G06F 3/01* (2006.01)
*A61B 6/03* (2006.01)
*G06K 9/62* (2006.01)
*G06F 3/03* (2006.01)

(52) U.S. Cl.
CPC ............ *A61B 6/0492* (2013.01); *A61B 6/467* (2013.01); *A61B 6/469* (2013.01); *A61B 6/488* (2013.01); *G06F 3/017* (2013.01); *G06F 3/0304* (2013.01); *G06K 9/6253* (2013.01); *G06K 2209/051* (2013.01)

(56) References Cited

U.S. PATENT DOCUMENTS

| | | |
|---|---|---|
| 2002/0118280 A1 | 8/2002 | Medlar et al. |
| 2004/0081341 A1 | 4/2004 | Cherek et al. |
| 2005/0025706 A1 | 2/2005 | Kagermeier |
| 2014/0153697 A1 | 6/2014 | Choi et al. |

OTHER PUBLICATIONS

Chinese Office Action for Chinese Application No. 201510588106.2, dated Dec. 27, 2017.
Chinese Office Action for Chinese Patent Application No. 201510588106.2, dated Aug. 27, 2018.

* cited by examiner

POSITIONING OF AN EXAMINATION TABLE RELATIVE TO A MEDICAL IMAGING APPARATUS

CROSS-REFERENCE TO RELATED APPLICATION

This application claims the benefit of DE 10 2014 218558.0, filed on Sep. 16, 2014, which is hereby incorporated by reference in its entirety.

BACKGROUND

An apparatus and method for the automated positioning of an examination table relative to a medical-technical imaging installation is provided.

The disclosed embodiments relate to a method and a user interface for the automated positioning of an examination table relative to a medical-technical imaging installation, in particular, a radiological imaging installation such as a computed tomography installation (CT) or a C-arm X-ray apparatus.

For planning a radiological examination, for example in computed tomography, an overview recording of the examination region is created. The overview recording is also referred to as a topogram. The topogram is the basis of the anatomical planning for the subsequent diagnostic scans. Furthermore, the topogram may be used to derive diverse parameters for automatically optimizing the examination protocol.

At present, a recording region (also referred to as scan region) may be positioned by manual selection of a start line and an end line of the recording region that are marked by a light beam localizer with laser marking lines on a patient or examination object lying on an examination table (patient couch) of the imaging installation. The examination table is movable in the longitudinal direction (z-direction) relative to a scanner (e.g. the gantry of a CT installation). The longitudinal axis of the patient may be generally parallel to the longitudinal direction of the examination table, and the examination table is often situated outside the scanner. If the start and end lines extend in the width direction (x-direction) of the examination table, the recording region may be defined in the longitudinal direction of the patient.

In order to create the overview recording, the patient has to adopt a suitable position on the examination table. The operator thereupon moves the table into a suitable start position by movement commands in order to record the organ or body region to be examined. The start position is reached when the anatomical start point sought becomes congruent with a laser line in the gantry. The laser line marks the plane in which the scan begins.

One conventional technique when determining the start point is feeling anatomical regions. By manually feeling the patient, the operator acquires information about the position of anatomical landmarks (e.g. the hip bone). Feeling becomes necessary if the patient's anatomy is hidden by bedding, clothing or medical apparatuses or no anatomical landmarks are visible, in principle, on account of the organ to be examined. The tactile information is transmitted into a visually detectable position by the position of the fingers. The start point of the overview recording is derived therefrom.

After the localization of the landmark and identification of the start point, the operator memorizes the anatomical landmark identified from manual examination, the start point resulting from the manual examination, or marks the corresponding location with a suitable aid.

It is known to compensate for positioning that initially is still inaccurate by manual readjustment by horizontal movements of the table. Accordingly, the operator uses a laser light beam localizer to visually monitor whether the position sought in the scan plane has been reached.

SUMMARY AND DESCRIPTION

It is an object of the present disclosed embodiments to provide a user interface and a method for the automated positioning of an examination table relative to a medical-technical imaging installation enabling precise and fast positioning.

Objects of the disclosed embodiments are achieved by a an apparatus including at least one camera aligned with an examination table. The apparatus may include a display and operating unit designed for outputting the camera image. The operation of the apparatus may be controlled by at least one microprocessor, programmed for freezing the camera image on the display and operating unit in a manner temporally dependent on a first user interaction; defining reference location information on the examination table in the frozen camera image on the basis of at least one second user interaction; and moving the examination table or the medical-technical imaging installation with the aid of a positioning system, wherein the reference location information is brought to congruence with a recording region of the medical-technical imaging installation.

A method is provided with at least one camera aligned with the examination table. A display and operating unit outputs the camera image. The method may be controlled by at least one microprocessor. The method includes freezing the camera image on the display and operating unit in a manner temporally dependent on a first user interaction; defining reference location information on the examination table in the frozen camera image on the basis of at least one second user interaction; and positioning the examination table or the medical-technical imaging installation with the aid of a positioning system, wherein the reference location information is brought to congruence with a recording region of the medical-technical imaging installation.

The advantages mentioned below need not necessarily be afforded by the all the embodiments. Advantages may also be afforded only by individual embodiments and/or variants.

The apparatus and the method enable a user to freeze the camera image by a first user interaction. Afterward, the user may define reference information in the frozen camera image by a second user interaction. The reference location information is, for example, a start line for a region of a patient to be scanned, or the region to be scanned itself.

The apparatus and the method obviate the need for the user to remember and visually track the reference location information as a point on a sheet with small specific surface features above a patient while the examination table and the reference location information move into a gantry while the user also observes and monitors the patient himself/herself and possibly also the cabling for the latter during the movement of the table. Since the movement of the patient into the gantry tube significantly restricts the view of the remembered point on the sheet and the visual monitoring subsequently has to be carried out in the center of the gantry tunnel, corrections under a laser light localizer are inconvenient, time-consuming, and additional precautions are necessary to provide that the patient is not disturbed by the laser light localizer.

By contrast, defining the reference location information in the frozen camera image is significantly more practical, mentally less taxing, and less susceptible to errors. Moreover, the user may position helpful markings in the camera image before freezing the latter. By way of example, the user may point with a finger at an anatomical landmark on the patient and use the finger pointing frozen in the camera image to position the reference location information.

In accordance with one embodiment, a first user interaction is initiated by the user by actuating a foot-operated switch, actuating a switch of a mobile apparatus, actuating a switch on the examination table, making a voice command, or making a pointing gesture.

In one embodiment, the microprocessor recognizes a pointing gesture in the camera image and defines marking location information in a manner dependent on the recognized pointing gesture.

Pointing gestures are suitable for generating marking location information that the user has ascertained by touch. The reference location information may also be defined based on pointing gestures. The positioning accuracy is increased by the marking location information, and the handling of the reference location information is accelerated and simplified since the reference location need not be memorized.

The possibility of attaching physical markings to facilitate position tracking during the movement of the table is made more difficult by materials covering the patient (e.g., towels, clothing). Markings on the patient's skin are not tolerated by the patient in the many examination cases. In the disclosed embodiments, marking location information is advantageously provided by virtual marking that may replace physical markings.

The marking location information is not affected by displacement of a covering of the patient (e.g. sheets or towels) since the marking location information visible in the camera image relates to a position on the object to be examined or on the examination table and not to the position of a cover. The disclosed embodiments are therefore invariant to a displacement of the cover and enable high planning fidelity in the positioning.

Problems that arise with the use of a camera image for positioning purposes may also be solved by the marking location information. If the relevant anatomical position for the organ or body region at issue may not be recorded by the existing camera perspective (e.g., the object of interest lies in a plane orthogonal thereto and may not be identified by the user in the camera image) then the disclosed embodiment may be used to fetch hidden positions into the plane of the camera perspective by the pointing gesture recorded in the camera image as marking location information. Particularly advantageously, such hidden positions may be ascertained by touch laterally with respect to the camera perspective and then converted into marking location information by the pointing gesture.

The marking location information is, for example, a start line for a recording region of a computed tomography apparatus or the recording region itself. The marking location information may be stored and thereby provided as a virtual marker for repeated positioning activities and the like.

The microprocessor is programmed, for example, to process an algorithm for recognizing the pointing gesture that may search the camera image for a pointer-type object projecting into the image from the side, above, or laterally with respect to the patient. Such a pointing gesture may readily be recognized and distinguished from other objects.

In accordance with one embodiment, the microprocessor provisionally defines the reference location information at a defined distance from the marking location information. Alternatively, the microprocessor provisionally defines the reference location information in accordance with the marking location information. Accordingly, the reference location information may be pre-allocated with the marking location information, such that the latter only has to be confirmed by the user.

In one embodiment, the microprocessor detects a displacement of the reference location information by a second user interaction. Alternatively or additionally, the microprocessor detects a confirmation of the reference location information by the second user interaction. The user may also adapt the reference location information, if appropriate, by displacing it on the display and operating unit.

In accordance with one embodiment, the microprocessor may store the reference location information and/or the marking location information as a point, as a line, or as an area in two-dimensional space. The microprocessor may store the reference location information and/or the marking location information as a plane or as a volume in three-dimensional space. The microprocessor may represent the reference location information and/or the marking location information as a movable positioning graphic, in particular as a line, as a pair of parallel lines, or as a rectangle over the frozen camera image on the display and operating unit. The microprocessor displaces the reference location information in a manner dependent on the second user interaction above the frozen camera image on the display and operating unit. The display and operating unit may be a touchscreen.

In one embodiment, the reference location information and/or the marking location information two-dimensionally or three-dimensionally map(s) a region such as an organ. The organ region may subsequently be brought to congruence with the recording region of the medical-technical imaging installation by the positioning. An organ region to be scanned of a patient may be displayed as marking location information and/or reference location information on the display and operating unit. By way of example, an anatomical patient model may be created based on a camera image that is used to infer the information regarding the organ selected by the pointing gesture of the user. The organ is represented on the display and operating unit and is marked visually as marking location information and/or reference location information.

In accordance with one embodiment, the microprocessor recognizes the pointing gesture in the frozen camera image. The user may freeze the camera image by the first user interaction, while pointing with the finger or with the hand at a location on the patient, for example, as a pointing gesture.

For example, a user's hand gesture used be evaluated as a pointing gesture indicating the marking location information on the examination table. If the pointing gesture is evaluated when the camera image is frozen, the microprocessor does not have to decide whether and at what point in time a pointing gesture was intended by the user. Accordingly, the programming of the microprocessor is considerably simplified. Since a real-time capability of the recognition is not necessary, it is possible to implement more complex algorithms for gesture recognition.

The point in time that the pointing gesture is valid is unambiguously defined by the freezing of the camera image and is clearly evident to the user, since the user sees the pointing gesture (and the marking location information and/or reference location information derived therefrom) in the frozen camera image. Advantageously, the user may directly track the effect of his/her pointing gesture. A sensed loss of control with free gesture control is thus counteracted.

In one embodiment, the microprocessor continuously recognizes a pointing gesture in the camera image before the camera image is frozen. The microprocessor continuously visually outputs the respectively recognized pointing gesture and/or location information derived therefrom on the display and operating unit. The microprocessor defines marking location information based on the pointing gesture recognized at the point in time of the first user interaction. The pointing gesture may be recognized in real time. The camera image that has not yet been frozen gives a real time indication of whether a pointing gesture was recognized and where the marking location information would be. However, the marking location information is stored only when the camera image is frozen.

In accordance with one embodiment, the microprocessor continuously evaluates the camera image before the camera image is frozen. The microprocessor freezes the camera image on the display and operating unit as soon as the microprocessor recognizes the pointing gesture. The pointing gesture may be a first user interaction. The marking location information may be generated efficiently because the user, after feeling an anatomical landmark, may conveniently leave his/her finger as a pointing gesture directly on the position found in order to generate the marking location information, e.g., the feeling finger simultaneously performs the pointing gesture. The identification of the marking location information is therefore accelerated.

In one embodiment, the microprocessor recognizes a two-handed gesture as the pointing gesture, and the marking location information describes a region to be scanned. The region to be scanned is subsequently brought to congruence with the recording region of the medical-technical imaging installation by the positioning. One hand of the user marks the start position and the other hand marks the end position of the scan and, the user freezes the camera image by a foot-operated switch. Alternatively, the two-handed gesture itself may cause the freezing of the camera image without additional action.

On the computer-readable data carrier there is stored a computer program that executes the method if it is processed in the microprocessor. The computer program executes the method while it is being processed in the microprocessor.

The scope of the disclosed embodiments is defined solely by the appended claims and is not affected to any degree by the statements within this summary. The present embodiments may obviate one or more of the drawbacks or limitations in the related art.

BRIEF DESCRIPTION OF THE DRAWINGS

Exemplary embodiments of the disclosed embodiments are explained in greater detail below with reference to figures. In the figures, identical or functionally identical elements are provided with the same reference signs, unless indicated otherwise.

In the figures.

DETAILED DESCRIPTION

Particularly in the case of CT apparatuses, an unnecessary radiation burden on the patient is to be avoided. Therefore, irrespective of whether a recording region, an overview recording, or a region for direct recording of the diagnostic imaging must be determined, the recording region should be chosen to be as small as possible, but the region of interest (ROI) should be covered completely. The user or operator of the installation is able to accurately recognize which anatomical regions of the patient are detected by the present setting to determine whether the ROI lies completely in the recording region. An erroneous setting leads to X-ray radiation emitted to the patient unnecessarily if the recording region is considerably larger than the ROI or if the recording region is smaller than the ROI, requiring the scanning process to be repeated.

Figure 1:
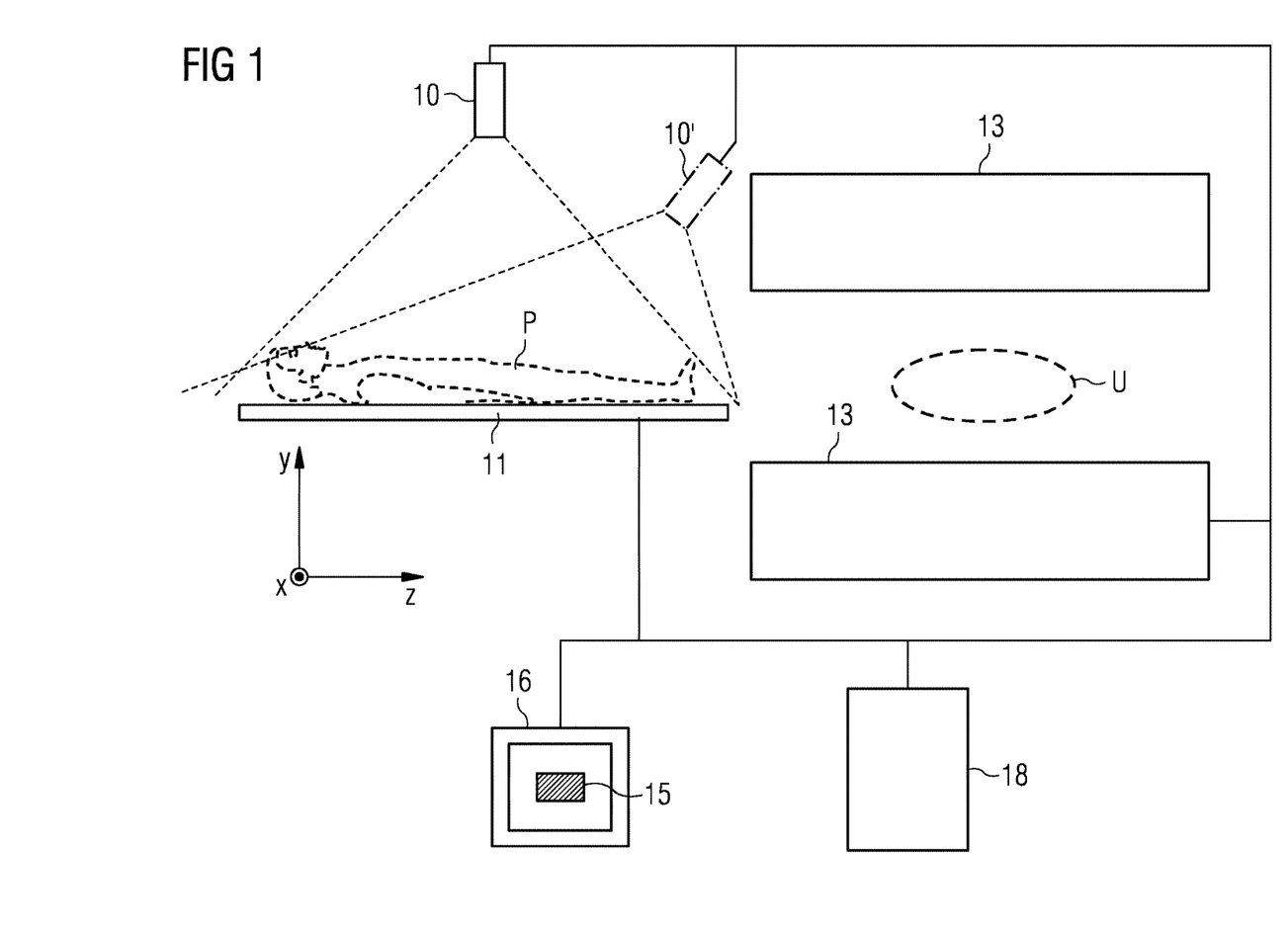
FIG. 1 illustrates one embodiment of a schematic construction of a user interface for the automated positioning of an examination table relative to a medical-technical imaging installation.

FIG. 1 illustrates a schematic construction of a device according to an embodiment including a schematically illustrated medical-technical imaging installation 13, for example a magnetic resonance apparatus or a computed tomography apparatus, with an examination volume U of known spatial position and extent.

A movable examination table 11 with a patient P situated thereon may be introduced into the medical-technical imaging installation 13. Alternatively, the medical-technical imaging installation 13 may be moved on rails above the examination table 11. The examination table 11 is spatially assigned a camera 10 for recording a camera image 15 of the examination table 11, the camera being arranged perpendicularly above the examination table. A display and operating unit 16 connected to the camera 10 and the medical-technical imaging installation 13 is designed for displaying the camera images 15. An alternative camera 10 may be arranged on the medical-technical imaging installation 13 and aligned with the examination table 11.

The display and operating unit 16 and a microprocessor 18, may be incorporated into or connected to camera 10, examination table 11, medical-technical imaging installation 13, and display and operating unit 16, enabling an identification and/or verification of body regions to be examined in the camera image 15. The microprocessor 18 additionally determines the spatial position of the identified body regions, calculates a travel distance, and controls the movement of the examination table 11 or of the medical-technical imaging installation 13 in the z-direction in accordance with the calculated travel distance.

The display and operating unit 16 is, for example, a personal computer or a workstation with screen, keyboard and mouse, a touchscreen or a tablet, and may also communicate wirelessly with the other components. The camera 10 may also be arranged laterally with respect to the examination table 11.

The user interface shown in FIG. 1 supplements the medical-technical imaging installation 13 by the camera 10 and may permanently record a camera image of the patient P or of any other object on the examination table 11. The camera image is forwarded to the display and operating unit 16, where a user may view the camera image and graphically define reference location information describing a region to be scanned.

Afterward, the examination table 11 or the medical-technical imaging installation 13 is positioned such that the reference location information is brought to congruence with the examination volume U. The reference location information may be positioned at the edge of the examination volume U if the reference location information itself has no extent in the z-direction. For example, the reference location information may define only a start line in the x- or y-direction or a start plane perpendicular to the z-axis. The reference location information may be conveyed in such a way that the reference location information is brought to congruence with a laser line of a laser light localizer in a gantry of the medical-technical imaging installation 13.

The user interface provides a function for freezing the camera image. The user feels an anatomy at issue on the patient P in order to decide the point on the body of the patient P that is to be marked. Then, the user points at the desired position with one of his/her fingers or some other aid (e.g. a pencil).

A first user interaction may then cause the user interface to freeze the camera image. A suitable, initial image of the patient P situated on the examination table 11 is visible in the frozen camera image 15 output on the display and operating unit 16. The user's finger or the aid used by the user to point at the desired position may be readily visible in the frozen camera image 15. The correspondingly identified location on the body of the patient P is thus stored in the frozen camera image 15 and provides marking location information, e.g., a visual marker. On the basis of the marking location information, the user may then also determine the reference location information, e.g. the target point of the positioning.

Moreover, the marking location information remains permanently available for further use throughout the diagnostic imaging process as long as the patient P does not move significantly. Significant movement of the patent P would necessitate a correction.

A second user interaction may accept the marking location information as the reference location information or adjust the reference location information by displacement on the display and operating unit 16.

The first and/or second user interaction(s) may be implemented by keyboard or mouse input, by pressing switches, or by touching a touchscreen, by voice input, by facial expression, and/or by gesture movements of the user.

Figure 2A:
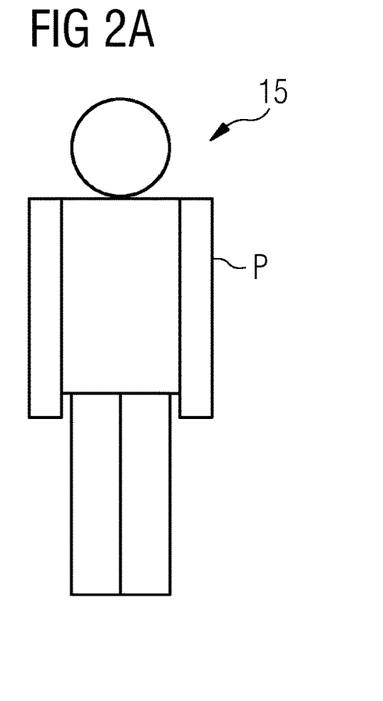
FIG. 2A illustrates an example frozen camera image of a patient with non-visible lateral landmarks.

FIG. 2A illustrates a plan view schematic illustration of a patient P such as is imaged in a frozen camera image 15. Anatomical landmarks that are not visible in the plan view may be recognized or ascertained by touch on the patient P laterally with respect to the plan view perspective.

Figure 2B:
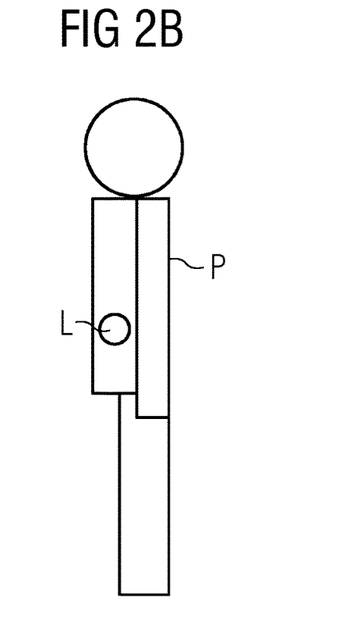
FIG. 2B illustrates an example of a side view of the patient with a visible landmark.

FIG. 2B illustrates one such landmark L that may be ascertained by touch only laterally on the patient P.

Figure 3A:
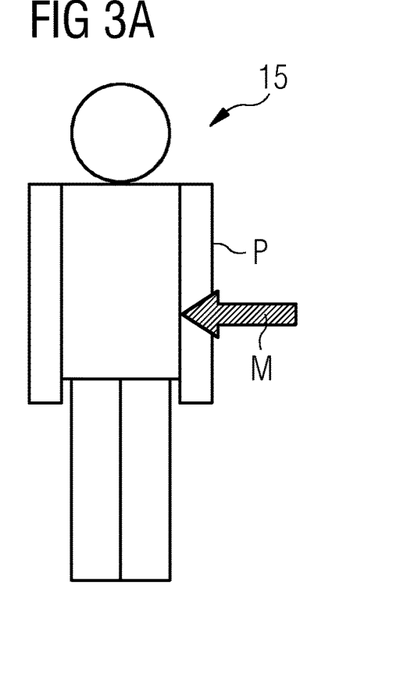
FIG. 3A illustrates an example of a frozen camera image of the patient depicting the lateral landmark from FIG. 2B made visible by marking location information.
Figure 3B:
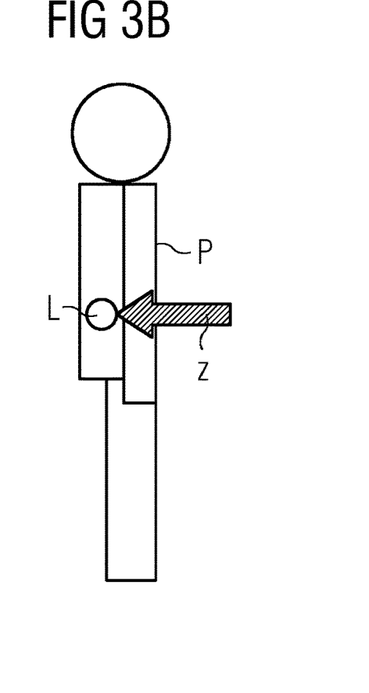
FIG. 3B illustrates an example of a side view associated with FIG. 3A depicting the landmark made visible by a pointing gesture.

In FIG. 3B, the landmark L is identified by a pointing gesture Z by a user, wherein the pointing gesture Z is performed in such a way that the gesture Z may clearly be recognized even from above in the frozen camera image 15 of the patient P as shown in FIG. 3A. Marking location information M may be generated based on the pointing gesture Z that may be used for planning the region to be scanned and in particular for defining the reference location information.

The object portion of the patient P that is orthogonal to the camera perspective and hidden in the camera image is also visible to the user on the examination table on account of his/her viewing angle. The user may thus recognize anatomical or other significant landmarks that may not be identified solely through the camera image. The pointing gesture Z and the marking location information M may be used to visualize such landmarks L in the frozen camera image 15. The landmark L localized laterally on the patient P is thus projected into the plane of the camera recording.

Landmarks L that are situated on the front side of the patient P in the field of view of the camera may also be identified by the pointing gesture Z in the frozen camera image 15 and be provided with marking location information M. In particular, landmarks L may not be recognized directly visually under a cover, but rather have to be ascertained by touch, for example the hip bones.

Figure 4:
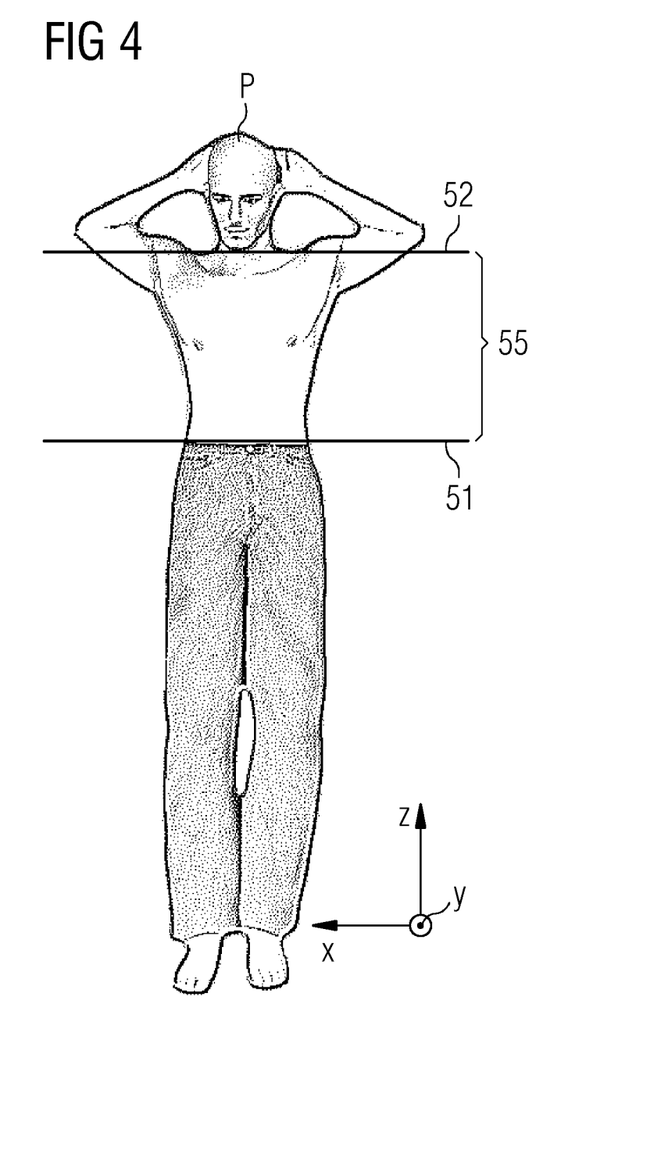
FIG. 4 illustrates an embodiment of a determination of a recording region for a patient.

FIG. 4 illustrates a patient P for whom a recording region 55 to be scanned is intended to be defined. The recording region is intended to be brought to congruence with an examination volume of the medical-technical imaging installation by suitable positioning of the examination table or of the medical imaging installation. The recording region 55 may be defined by a start line 51 and an end line 52.

Figure 5:
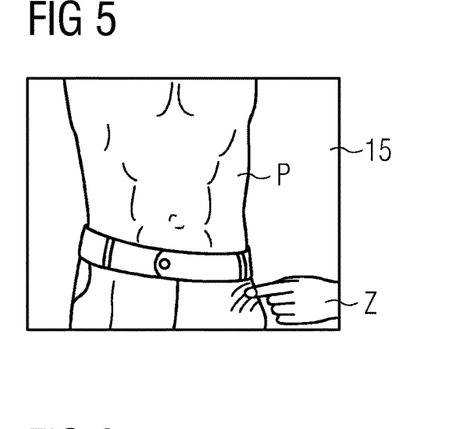
FIG. 5 illustrates an example of a pointing gesture that makes a landmark visible in a frozen camera image of a patient.

FIG. 5 illustrates a frozen camera image 15 of a patient P depicting a user's left hand pointing at a left hip bone of the patient P by a pointing gesture Z. A first user interaction, for example the actuation of a foot-operated switch, a voice command, an actuation of a switch on the examination table, a wired or wireless switch held in the other hand, or by means of the pointing gesture Z itself may cause the camera image to freeze and/or to become the frozen camera image 15. The user carries out the first user interaction deliberately at the point in time that the user's pointing gesture Z is visible in the camera image completely and correctly from the user's viewpoint.

Since the user may freely select the point in time that the camera image is frozen himself/herself by the first user interaction, the user has no uncertainly about whether and at what point in time his/her pointing gesture Z is recognized by the system. Furthermore, a microprocessor that evaluates the frozen camera image 15 does not have to decide whether or at what point in time the user wanted to effect the pointing gesture Z, rather the algorithm used may assume that the pointing gesture Z is already present in the frozen camera image 15. The algorithm for recognizing the pointing gesture Z may examine the frozen camera image 15 for objects projecting into the frozen camera image 15 from the right with a pointed contour. If a 3D camera or some other 3D sensor is used and depth image information is available for the frozen camera image 15, the microprocessor may search in a targeted manner, for the pointing gesture Z or for objects situated on or above the surface of the patient P.

The above-described recognition of the pointing gesture Z in the frozen camera image 15 is one possible embodiment. One alternative embodiment allows the microprocessor to carry out a continuous recognition of or search for the pointing gesture Z in the camera image before the camera image is actually frozen. Continuous recognition of visual information may identify that no pointing gesture is recognized at present, may identify the respective current position of the recognized pointing gesture, and may be output continuously to the user on a display and operating unit. Here, too, the camera image is frozen at the point in time of the first user interaction, as generated in the frozen camera image 15 with the pointing gesture Z depicted in FIG. 5. Continuous recognition may allow the user to obtain a preview of whether a pointing gesture may be recognized and where the pointing gesture is situated in the camera image.

In one specific variant of this embodiment, the recognition of the pointing gesture Z by the microprocessor may be considered as the first user interaction, that is, the user deliberately freezes the camera image by the pointing gesture Z. One example of a pointing gesture Z causing the freezing of the camera image by holding the gesture for a period of three seconds.

In some variants, the pointing gesture Z may also be a two-handed gesture that may then be used directly to derive boundaries on two sides of the region to be scanned as marking location information and/or reference location information.

The way that the pointing gesture Z is recognized and frozen in the camera image 15 is of no importance for the following explanations concerning FIG. 6 to FIG. 9. The following explanations are thus applied to all above-described exemplary embodiments and variants.

Figure 6:
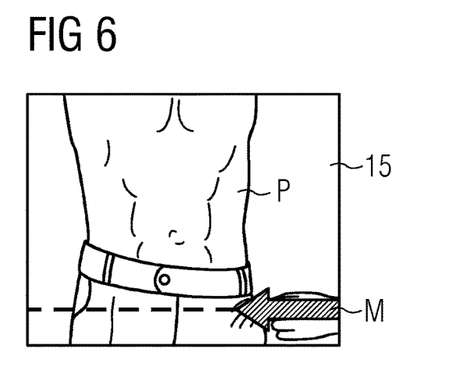
FIG. 6 illustrates an embodiment of marking location information that makes a landmark visible in a frozen camera image of a patient.

FIG. 6 illustrates the frozen camera image 15 of the patient P from FIG. 5. A microprocessor may be situated locally in a mobile tablet, in an arithmetic and control unit, in a server, or in the Cloud. The microprocessor may generate marking location information M in the frozen camera image 15 after recognizing the pointing gesture Z, the microprocessor visualizing the marking location information visually as an arrow above the pointing gesture in the frozen camera image 15. The arrow of the marking location information M is extended by a dashed line defining, for example, a start line for a region to be scanned on the patient P.

The marking location information M may be stored with the frozen camera image 15 and reused as often as desired, as long as the patient P does not move or is brought into the same position again in the event of renewed positioning on the examination table.

The marking location information M may also simultaneously be used as reference location information in order to define the region to be scanned on the patient P.

Figure 7:
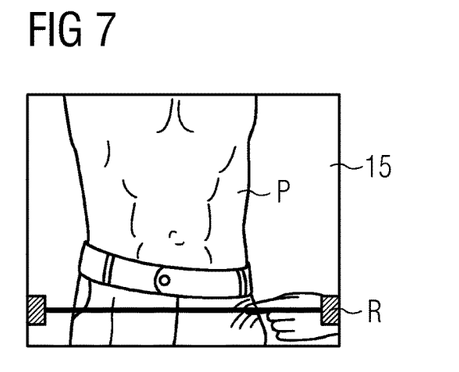
FIG. 7 illustrates an example of reference location information that is positioned in a manner corresponding to a pointing gesture in a frozen camera image of a patient.

FIG. 7 illustrates the frozen camera image 15 of the patient P after the user, by a second user interaction, has confirmed the marking location information M as reference location information R for defining a start line of the region to be scanned. The second user interaction may alternatively displace the reference location information R, illustrated as a horizontal line with contact points above the frozen camera image 15. The second user interaction is carried out for example by a keyboard and/or mouse on a personal computer that outputs the camera image 15. Alternatively, the second user interaction may be input by a touch input on a touchscreen displaying the frozen camera image 15. That is, the user may move the reference location information R by touching and dragging to the position desired by the user.

Figure 8:
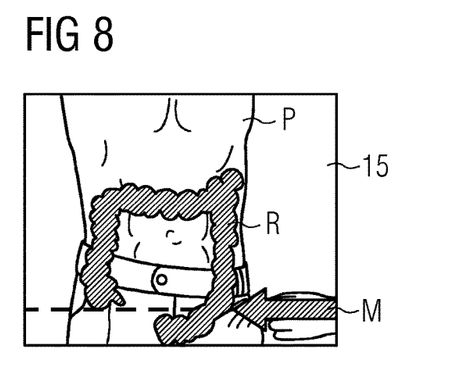
FIG. 8 illustrates an example of an organ selected as reference location information based on marking location information in a frozen camera image of a patient.

FIG. 8 illustrates that the reference location information R may also be represented differently as a superimposed visualization of an organ of the patient P in the frozen camera image 15, here the colon of the patient P. The organ to be visualized, defined as the region to be scanned by reference location information R, is determined directly on the basis of the marking location information M. In the example shown, the colon of the patient P is in direct proximity to the pointing gesture Z effected by the user in the frozen camera image 15.

The second user interaction, for example a voice command, keyboard input, mouse click, or touchscreen input, may be used to select other organs as reference location information R and the selected organs may also be displayed above the frozen camera image 15, that are likewise situated in direct proximity to the marking location information M. The region to be scanned is then defined based on the last selected organ as reference location information R. In order to display the organs as reference location information R above the frozen camera image 15, a suitable computer program correlates the image of the patient P with an anatomical model of human beings, such that dimensions and positions of organs may be calculated appropriately for the proportions of the respective patient P and may be visualized at the correct location in the frozen camera image 15.

Figure 9:
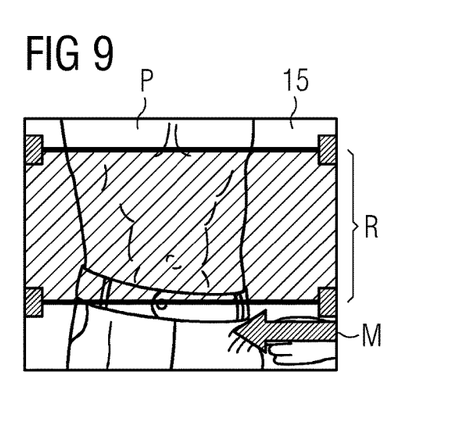
FIG. 9 illustrates an example of a recording region selected as reference location information based on marking location information in a frozen camera image of a patient.

FIG. 9 illustrates a further variant in the determination of the reference location information R with the aid of the marking location information M. The reference location information R is represented in the frozen camera image 15 of the patient P as a hatched region delimited by two horizontal boundary lines analogous to the start line 51 and end line 52 in FIG. 4. The horizontal lines are again provided with contact points allowing displacement in a vertical direction conveniently by mouse or touch input. In the embodiment shown in FIG. 9, although the operator has visualized the left hip bone of the patient P using the pointing gesture as marking location information M in the frozen camera image 15, the operator does include the hip bone itself in the region to be scanned, but rather adjusts the reference location information R to begin at the region a few centimeters above. The reference location information R may be adjusted by one or more movable positioning graphics serving as a positioning aid based on the marking location information M that was generated at an earlier point in time. The examination table or the medical-technical imaging installation is moved with the aid of a positioning system in such a way that the reference location information R is brought to congruence with an examination volume of the medical-technical imaging installation.

In a departure from the above-described exemplary embodiments, the reference location information R and marking location information M need not necessarily be represented as a line, organ, or area in two-dimensional space. Other examples for visualization are points in three-dimensional space, planes, or a volume in three-dimensional space that may run parallel to sectional planes of the medical-technical imaging installation.

The marking location information M and/or the reference location information R may be represented in the form of a solid or dashed start line and/or end line projected virtually onto the patient analogous to a light or laser marking. The marking location information M and/or the reference location information R may relate, inter alia, to the start line, to the end line, to both the start line and the end line, or to the recording region scanned thereby.

The marking location information M and the reference location information R may both be stored in an electronic memory, for instance a main memory or read-only memory. It is also possible to store multiple items of marking location information M for the same patient or different patients. However, the marking location information M may also be converted into the reference location information R, such that only one item of location information is retained in the memory at any point in time.

The components or assemblies of the user interface are signal-conductively connected to one another in a suitable manner in order to be able to cooperate in accordance with the method. The term, "signal-conductively" may be understood to mean not only an electrically conductive connection but also a wireless connection. In particular, the components or assemblies may also be interconnected via a bus system.

The methods described in detail above and also the user interface presented are non-restrictive exemplary embodiments that may be modified in a variety of ways by the person skilled in the art, without departing from the scope of the disclosed embodiments. The described exemplary embodiments, variants, and embodiments may also be freely combined with one another.

Although the disclosed embodiments have been described for use on a computed tomography installation, for example, advantageous use may be present on other medical-technical installations, such as for example: other X-ray-based installations, e.g. for creating conventional X-ray recordings or radiological examinations; magnetic resonance imaging apparatuses (MRI); installations for creating images on the basis of radionuclides, e.g. scintigraphy, positron emission tomography (PET), single-photon emission computed tomography (SPECT); installations for creating images on the basis of ultrasonic waves, e.g. sonography, color Doppler; installations for creating images on the basis of infrared radiation, e.g. diagnostic thermography; installations for creating images on the basis of electrical resistances or impedances, e.g. electrical impedance tomography (EIT); or installations for creating images on the basis of visible light, e.g. endoscopy, optical tomography.

Furthermore, the use of the indefinite article "a" or "an" does not preclude that the relevant features may also be present repeatedly. Likewise, the terms "unit" and "module" do not preclude that the relevant components includes a plurality of interacting sub-components, if appropriate, may also be spatially distributed.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

We claim:

1. An apparatus for automated positioning of an examination table relative to a medical-technical imaging installation comprising:
    at least one camera aligned with an examination table; and
    a display and operating unit, designed for outputting a camera image, including at least one microprocessor;
    the microprocessor configured to cause the apparatus to:
        continuously evaluate the camera image before the camera image is frozen;
        recognize a pointing gesture in the camera image;
        upon recognition of the pointing gesture, freeze the camera image on the display and operating unit in a manner temporally dependent on a first user interaction, wherein the pointing gesture is the first user interaction;
        define reference location information on the examination table in the frozen camera image based on at least one second user interaction; and
        move the examination table or the medical-technical imaging installation with aid of a positioning system, wherein the reference location information is brought to congruence with a recording region of the medical-technical imaging installation.

2. The apparatus of claim 1, wherein the microprocessor is further configured to cause the apparatus to:
    define marking location information based on the recognized pointing gesture.

3. The apparatus of claim 2, wherein the microprocessor is further configured to cause the apparatus to:
    provisionally define the reference location information at a defined distance from the marking location information; or
    provisionally define the reference location information in accordance with the marking location information.

4. The apparatus of claim 2, wherein the microprocessor is further configured to cause the apparatus to:
    detect a displacement of the reference location information by the second user interaction; or
    detect a confirmation of the reference location information by the second user interaction.

5. The apparatus of claim 2, further comprising:
    a touchscreen,
    wherein the microprocessor is further configured to cause the apparatus to:
        store the reference location information, the marking location information, or the reference location information and the marking location information as a point in two-dimensional space, a line in two-dimensional space, an area in two-dimensional space, a line in three-dimensional space, a plane in three-dimensional space, or a volume in three-dimensional space;
        represent the reference location information, the marking location information, or the reference location information and the marking location as a movable positioning graphic displayed above the frozen camera image on the display and operating unit; and
        displace the reference location information based on the second user interaction above the frozen camera image on the touchscreen.

6. The apparatus of claim 5, wherein the movable positioning graphic is a line, a pair of lines, or a rectangle.

7. The apparatus of claim 2, wherein the reference location information, the marking location information, or the reference location information and the marking location information two-dimensionally or three-dimensionally map(s) a region of an organ,
wherein the region of the organ is brought to congruence with the recording region of the medical-technical imaging installation by the positioning.

8. The apparatus of claim 2, wherein the microprocessor is further configured to cause the apparatus to:
recognize a two-handed gesture as the pointing gesture, wherein the marking location information, the reference location information, or the marking location information and the reference location information describe(s) a region to be scanned,
wherein the region to be scanned is brought to congruence with the recording region of the medical-technical imaging installation by the positioning.

9. An apparatus for automated positioning of an examination table relative to a medical-technical imaging installation comprising:
at least one camera aligned with an examination table; and
a display and operating unit, designed for outputting a camera image, including at least one microprocessor;
the microprocessor configured to cause the apparatus to:
continuously recognize a pointing gesture in the camera image before the camera image is frozen;
continuously visually output the respectively recognized pointing gesture on the display and operating unit;
define marking location information in a manner dependent on the pointing gesture recognized at a point in time of a first user interaction;
freeze the camera image on the display and operating unit in a manner temporally dependent on the first user interaction;
define reference location information on the examination table in the frozen camera image based on at least one second user interaction; and
move the examination table or the medical-technical imaging installation with aid of a positioning system, wherein the reference location information is brought to congruence with a recording region of the medical-technical imaging installation.

10. A method for automated positioning of an examination table relative to a medical-technical imaging installation, the method comprising:
continuously evaluating, by at least one microprocessor, a camera image before the camera image is frozen;
recognizing, by the at least one microprocessor, a pointing gesture in the camera image;
freezing, by the at least one microprocessor, the camera image on a display and operating unit upon recognition of the pointing gesture by the at least one microprocessor, wherein the freezing is temporally dependent on a first user interaction, and wherein the pointing gesture is the first user interaction;
defining, by the at least one microprocessor, reference location information on the examination table aligned with at least one camera in the frozen camera image based on at least one second user interaction; and
positioning the examination table or the medical-technical imaging installation with aid of a positioning system, wherein the reference location information is brought to congruence with a recording region of the medical-technical imaging installation.

11. The method of claim 10, further comprising:
defining, by the at least one microprocessor, marking location information based on the recognized pointing gesture.

12. The method of claim 11, further comprising:
provisionally defining, by the at least one microprocessor, the reference location information at a defined distance from the marking location information; or
provisionally defining, by the at least one microprocessor, the reference location information in accordance with the marking location information.

13. The method as claimed in claim 12, further comprising:
detecting, by the at least one microprocessor, a displacement of the reference location information by the second user interaction; or
detecting, by the at least one microprocessor, a confirmation of the reference location information by the second user interaction.

14. The method of claim 11, further comprising:
storing, by the at least one microprocessor, the reference location information, the marking location information, or the reference location information and the marking location information as a point in two-dimensional space, a line in two-dimensional space, an area in two-dimensional space, a plane in three-dimensional space, or a volume in three-dimensional space;
representing, by the at least one microprocessor, the reference location information, the marking location information, or the reference location information and the marking location information as a movable positioning graphic over the frozen camera image on the display and operating unit; and
displacing, by the at least one microprocessor, the reference location information in a manner dependent on the second user interaction above the frozen camera image on the display and operating unit.

15. The method of claim 14, wherein the movable positioning graphic is a line, a pair of lines, or a rectangle.

16. The method of claim 11, wherein the reference location information, the marking location information, or the reference location information and the marking location information two-dimensionally or three-dimensionally map(s) an organ region that is brought to congruence with the recording region of the medical-technical imaging installation by the positioning.

17. The method of claim 11, further comprising:
recognizing, by the at least one microprocessor, a two-handed gesture as the pointing gesture, wherein the marking location information, the reference location information, or the marking location information and the reference location information describe(s) a region to be scanned, that is brought to congruence with the recording region of the medical-technical imaging installation by the positioning.

18. A non-transitory computer readable medium including instructions that when executed are operable to:
continuously recognize a pointing gesture in a camera image before the camera image is frozen;
continuously visually output the respectively recognized pointing gesture on a display and operating unit;
define marking location information in a manner dependent on the pointing gesture recognized at a point in time of a first user interaction;
freeze a camera image on the display and operating unit, the freezing temporally dependent on the first user interaction;

define reference location information on an examination table aligned with at least one camera in the frozen camera image based on at least one second user interaction; and position the examination table or a medical-technical imaging installation with aid of a positioning system, wherein the reference location information is brought to congruence with a recording region of the medical-technical imaging installation.

* * * * *